(12) United States Patent
Laitinen

(10) Patent No.: US 6,493,076 B1
(45) Date of Patent: Dec. 10, 2002

(54) METHOD AND ARRANGEMENT FOR MEASURING WOOD

(75) Inventor: Jyrki Laitinen, Oulu (FI)

(73) Assignee: Andritz AG, Graz (AT)

(*) Notice: Subject to any disclaimer, the term of this patent is extended or adjusted under 35 U.S.C. 154(b) by 0 days.

(21) Appl. No.: 09/830,233

(22) PCT Filed: Oct. 27, 1999

(86) PCT No.: PCT/FI99/00899

§ 371 (c)(1),
(2), (4) Date: Apr. 24, 2001

(87) PCT Pub. No.: WO00/25115

PCT Pub. Date: May 4, 2000

(30) Foreign Application Priority Data

Oct. 28, 1998 (FI) .................................................. 982341

(51) Int. Cl.$^7$ ......................... G01N 21/00; G01N 21/88; G01J 3/00; G01J 3/46
(52) U.S. Cl. ................................ 356/237.2; 356/237.1; 356/300; 356/402; 250/559.45; 250/559.46
(58) Field of Search .......................... 356/237.1, 237.2, 356/402–425, 300–334, 431, 369; 250/559.45, 559.42, 559.46; 209/555; 428/528; 162/260; 700/230

(56) References Cited

U.S. PATENT DOCUMENTS

| | | | | |
|---|---|---|---|---|
| 3,389,789 A | * | 6/1968 | Watson et al. ................ 209/555 |
| 3,694,658 A | * | 9/1972 | Watson et al. ............ 250/559.42 |
| 3,976,384 A | * | 8/1976 | Matthew et al. ............... 356/431 |
| 4,402,604 A | * | 9/1983 | Nash ............................ 356/237.1 |
| 4,672,006 A | * | 6/1987 | McGraw ......................... 428/528 |
| 4,764,017 A | * | 8/1988 | Hirvonen ........................ 356/369 |
| 4,895,019 A | | 1/1990 | Lehmikangas et al. ........... 73/63 |
| 4,897,159 A | * | 1/1990 | Bone et al. ..................... 162/260 |
| 4,984,172 A | * | 1/1991 | Luminari ........................ 700/230 |
| 5,274,244 A | | 12/1993 | Johansson et al. ............. 250/563 |

FOREIGN PATENT DOCUMENTS

| | | |
|---|---|---|
| EP | 0 831 320 A2 | 3/1998 |
| FI | 90918 | 3/1993 |
| SE | 466 420 | 2/1992 |
| WO | WO 95/31710 | 11/1995 |

* cited by examiner

*Primary Examiner*—Georgia Epps
*Assistant Examiner*—Gary O'Neill
(74) *Attorney, Agent, or Firm*—Alix, Yale & Ristas, LLP

(57) ABSTRACT

The invention relates to a method and arrangement for measuring the quality of wood. The wood comprises not only a pure body but also components of bark and knots, having optical properties different from those of the pure body. Barked trees (308) are turned into wood powder (322). The wood powder (322) is illuminated with optical radiation and the radiation is received by means of a camera (330). The camera (330) transmits a signal consistent with the radiation reflected from or passed through the wood powder (322) to a computer (332) which, by means of the optical properties of the wood powder (322), determines the amount of bark, knots, and/or defective wood present in the wood.

34 Claims, 4 Drawing Sheets

METHOD AND ARRANGEMENT FOR MEASURING WOOD

CROSS REFERENCE TO RELATED APPLICATIONS

This application is a 371 of PCT/FI99/00899 Oct. 27, 1999 now WO 00/25115.

FIELD OF INVENTION

The present invention relates to the measurement of wood, especially by means of optical radiation.

BACKGROUND OF INVENTION

In mechanical and chemical forestry, one of the most important wood handling processes is the barking of logs. In the production of energy as well, the handling of logs is usually begun by barking and the amount of bark has an impact on the burning process in terms of its regulation and efficiency. In the production of pulp, the barked trees are first chipped, whereafter the chips proceed to a pulp digester. The bark remaining on chips deteriorates the quality of pulp being produced and causes a need of adjustment in the digestion process. Mechanical pulp is produced by grinding or refining. In grinding, the barked log is pressed against a grindstone. In refining, the barked logs are first chipped and the chips are refined between two rotary wheels. However, it is not worth while to bark the logs too thoroughly, as a result of this is the removal of pure wood material along with the bark, leading to losses of energy and material. It has been a common attempt to regulate the barking process in view of optimizing the amount of bark in wood chips. The amount of bark typically accepted in a pulp mill is less than 0.5%–1%, and in a paper mill even less than 0.1% of the total mass of refined or ground mechanical pulp. The adjustment of a barking process requires information about the purity grade or thoroughness of barking.

In prior art solutions, the purity grade of barking is measured by imaging the logs or chips to be barked and by applying various computer-based image processing programs for assessing the respective proportions of wood and bark. Indeed, there is such a distinction between bark and pure wood body that bark is usually darker than pure wood body. A problem in this type of method is that it is difficult to distinguish the dark bark for example from shadows. Moisture causes reflections, impeding the detection of bark material present in the chips or body. In addition, when measuring tree trunks, it is difficult to make a distinction between the pure wood material and the bark as a result of the geometrical patterns of a wood surface. The problem is particularly pronounced when the amount of bark is small.

In another prior art solution, the purity grade of barking has been measured by estimating the proportion of pure body material in barking refuse. However, the measurement does not correlate particularly well with the bark remaining affixed to a tree trunk, since the barking process makes it necessary to break dry wood more than moist wood. Thus, the barking refuse of dry wood contains a greater amount of pure body material than the barking refuse of moist wood, even though both logs would have an equal amount of bark affixed thereto.

BRIEF DESCRIPTION OF INVENTION

The invention seeks to provide such a method, and such an arrangement for implementing the method, that the above problems can be solved.

It is an object of the invention to provide a method for measuring the quality of wood, in which method the wood is constituted by timber which, in addition to a pure body, includes at least a bark component and knot components, which differ from the pure body in terms of optical properties thereof, the method involving the barking of logs. Furthermore, the method of the invention comprises turning at least some of the barked trees into wood meal or powder; exposing the wood meal to optical radiation; and measuring the quality of wood by means of the optical radiation.

It is another object of the invention to provide a measuring arrangement for the quality of wood, wherein the wood refers to timber which, in addition to a pure body, includes at least a bark component and a knot component, having optical properties different from those of the pure body, said measuring arrangement comprising a stripper for the barking of logs. Furthermore, in the arrangement of the invention, the measuring arrangement is adapted to produce wood meal or powder from barked trees; the measuring arrangement comprises a detector responsive to optical radiation; the measuring arrangement comprises a measuring device; and the detector is adapted to receive optical radiation coming from the direction of wood meal or powder and to carry a signal responsive to the optical radiation to the measuring device, and the measuring device is adapted to measure the wood meal by means of an optical-radiation based signal coming from the detector, and to determine the quality of wood.

A number of benefits are gained by the method and system of the invention. The amount of bark, knots, and/or defective wood in timber can be reliably measured without being interfered by the shape, shadows, or moisture (moisture-caused reflections) of tree trunks. Furthermore, the barking process and for example the digestion of chemical pulp can be optimally controlled according to the quality of wood.

BRIEF DESCRIPTION OF DRAWINGS

The invention will now be described more closely in conjunction with preferred embodiments, with reference made to the accompanying drawings, in which.

DETAILED DESCRIPTION OF INVENTION

The invention offers a solution which is particularly applicable to wood handling processes used in mechanical and chemical forest industry. In addition, the invention provides a solution, which is applicable in sawmills and wood-consuming power production facilities requiring accurate knowledge about the quality of wood being used.

Figure 1:
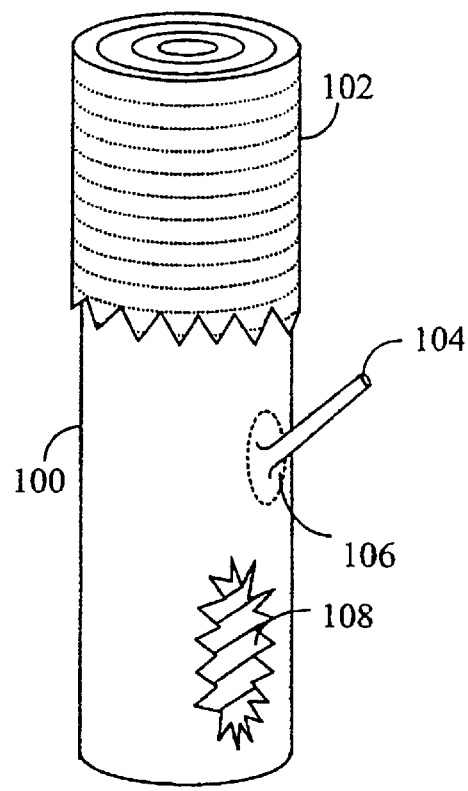
FIG. 1 shows a piece of wood.

Reference is first made to a block of wood, which is shown in FIG. 1. The block of wood may be for example a log coming into the barking plant of a pulp mill. The block of wood comprises a pure body 100, a bark 102, a branch 104, a knot 106, and a defective wood 108. The exemplified block of wood is for example a log of pine or spruce. The knot 106 refers to a zone affected by the branch 104. It is essential for the solution of the invention that the bark 102 or any wood material other than the pure body 100 be optically distinct from the pure body 100. Typically, the knot 106 referred to as a zone affected by the branch 104 is optically perceivable from the pure body 100. Likewise, the defective wood 108 has an optical behaviour different from that of the pure body 100. The defective wood 108 may be mechanically damaged or it may be sick, for example rotten.

Figure 2:
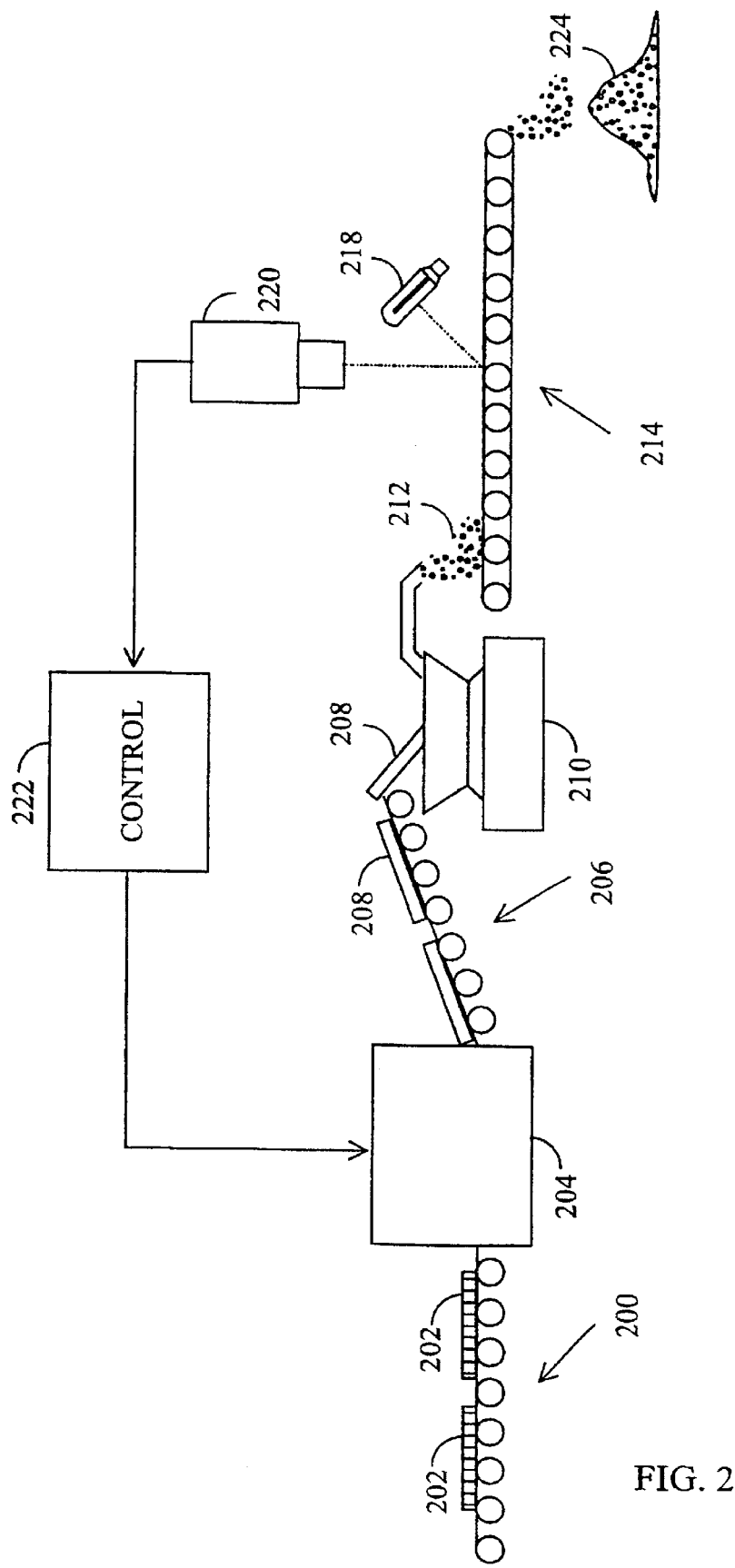
FIG. 2 shows a measuring arrangement.

The solution of the invention will be examined now in general terms, with reference made to FIG. 2. The solution of the invention comprises a feeder 200, possibly a conveyor belt, which carries incoming unbarked logs 202 to a stripper 204. The stripper 204 may be for example a barking drum. A second feeder 206, for example another conveyor belt, is used for carrying barked logs 208 to a sawdust refiner 210 for turning the logs 208 into a powder or meal 212. Regarding the classification of its size, the powder is preferably not above the centimeter class. The powder 212 is preferably the same type as sawdust or cutter chips. The powder 212 has a virtue of being homogeneous and the powder 212 reflects optical radiation almost totally diffusively, thus avoiding the problems caused by reflection. From the sawdust refiner 210 the powder or meal 212 progresses onto a measuring deck 214, which may be a conveyor belt or a stationary platform. As soon as the powder 212 reaches a measurement site 216, the powder 212 is lighted with an illuminator 218. The illuminator 218 comprises preferably a fluorescent tube, but the illuminator can be constituted by one or more identical or different sources of optical power, which may be any narrow-or broadband, continuous or pulse-repeated sources of optical power, such as for example filament lamps, LEDs, and lasers. Since the measurement is preferably conducted indoors, for example in an industrial hall, the sample is most preferably lighted with the very same ceiling-mounted indoor illuminator that is used for lighting the entire hall. It is also possible to use daylight for lighting. At the measurement site 216, the powder 212 is measured for at least one optical property, such as for example darkness, colour, and spectral distribution. In the proximity of the measurement site 216 is located a detector 220, which is responsive to optical radiation transmitted by the illuminator 218. The powder 212 reflects optical radiation to the detector 220, which supplies a measuring block 222 with a signal proportional to optical radiation received thereby. Typically, the detector 220 comprises a video camera or a line camera, which is trichromatic, black-and-white, digital, or analogical. If the detector 220 is analogical, the measuring block 222 requires a digitizing board for facilitating digital signal processing. The signal transmitted by the detector 220 is used by the measuring block 222 for measuring the powder 212 for its reflection density or darkness, colour, and/or spectral distribution with an image processing program. In a solution of the invention, the measuring block 22 is preferably used for controlling the stripper 204, as well. If, for example, the powder 212 has a reflection density or degree of darkness which is far too light (hypothesis: the bark 102 is dark and the pure body 100 is light), the stripper 204 will have its barking efficiency reduced. On the other hand, if the powder 212 has an excessively high reflection density, the barking efficiency will be increased (in a barking drum, the barking time is increased).

Figure 3:
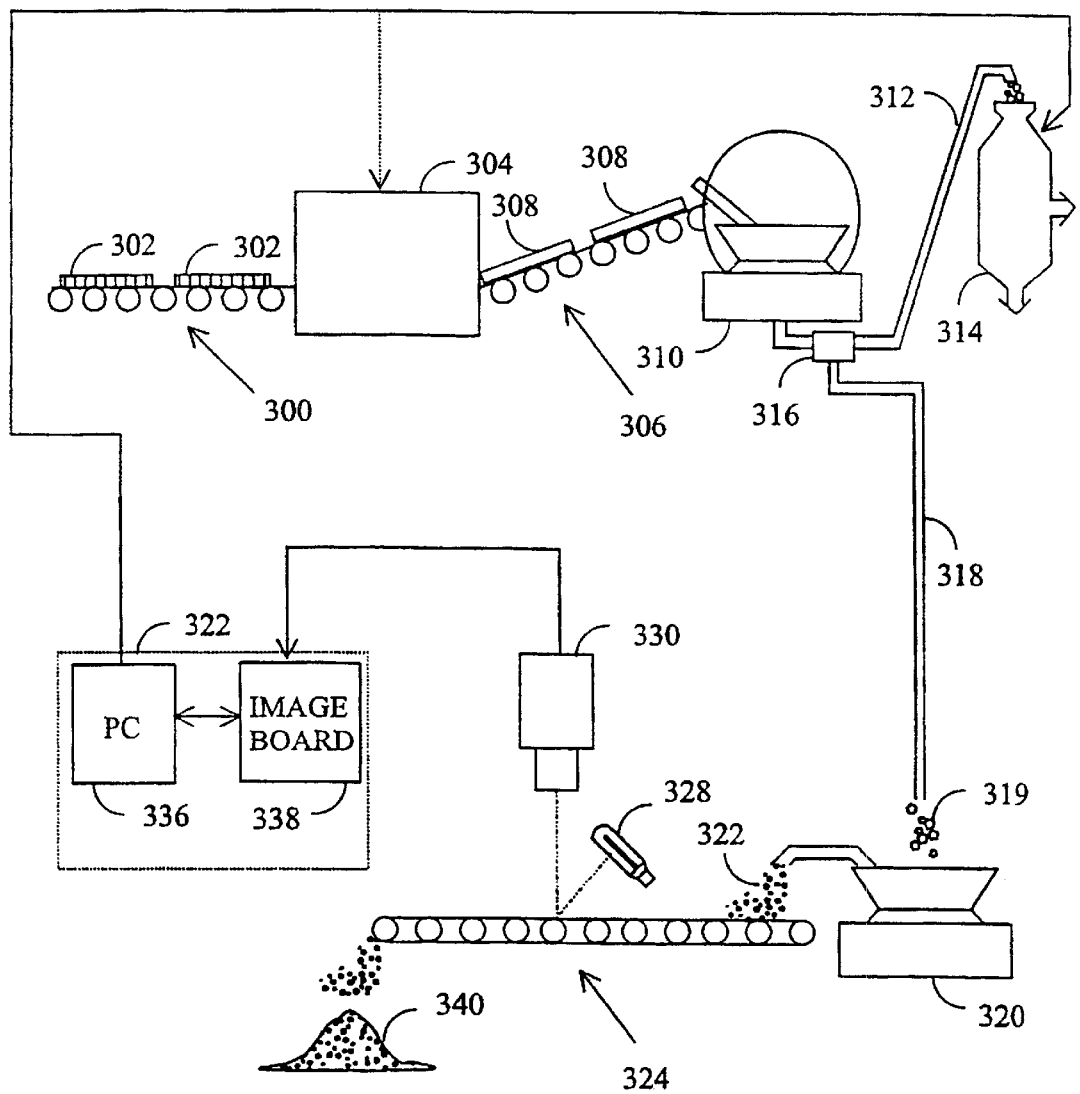
FIG. 3 shows a measuring arrangement.

The solution of the invention will now be studied as applied in conjunction with a pulping process, as shown in FIG. 3. In this case, as well, unbarked logs 302 are delivered for example on a conveyor belt 300 to a stripper 304. Barked logs 308 are carried on a conveyor belt 306 to a chipper 310 for turning the barked trees into chips. For the most part, the chips are carried along a transfer line 312 to a pulp digester 314. In practice, the transfer line 312 may be provided with an intermediate storage (not shown in FIG. 3), but this is not essential as far as the invention is concerned. A chip sample 319 is picked up from the moving chips at a point 316 onto a sample line 318. The chip sample 319 constitutes a representative sample of the barked logs 308 as the chipper has chipped the trees into smallish chip fragments and mixed the chip fragments thoroughly. The chip sample is carried to a sawdust refiner 320, which is typically a mechanical, chip-breaking device. The sawdust refiner 320 turns the chips 319 into a powder or meal 322 suitable for a measurement, which is transferred onto a measurement deck 324. The measurement deck 324 is preferably a conveyor belt overlaid with a uniform layer of the wood meal or powder 322. Upon reaching the end of the conveyor belt, the wood meal 322 is dropped onto a heap of wood meal 340. The wood meal 322 is illuminated with optical radiation at least at a measurement site 326. The optical radiation is generated by an illuminator 328, which has already been described in conjunction with FIG. 2. It is a detector 330 which receives radiation reflected from or passed through the wood meal 326 and transmits, in accordance with the impact caused by the radiation, a signal to a measuring device 332, comprising at least a PC-computer 336. The detector 330 has already been described in conjunction with FIG. 2. Especially, if the detector 330 is an analogic camera, the measuring device 332 requires not only the PC-computer 336 but also a digitizing board 338 for converting an analogical signal to a digital one. The PC-computer 336 is provided with software for determining the wood meal 322 in terms of its reflection density, colour, and/or spectral distribution. In addition, the PC-computer 336 is functionally linked to the stripper 304 and/or the pulp digester 314, such that the information regarding the quality of wood obtained by measuring at least one optical property of the wood meal 322 could be used for driving or controlling the stripper 304 and/or the pulp digester 314 for the achievement of a more optimal barking result and/or pulping process. At its simplest, the fact is that the barking purity of the stripper 304 can be controlled by a measurement of the wood meal 322 for its reflection density, since the wood meal 322 has its reflection density varying essentially as a function of the amount of bark. For the most part, the same applies to the control of a pulping process, as well. In pulping, however, it is also important to have knowledge about the number of branches and the amount of defective wood. This information is obtained by measuring the wood meal or powder 322 for its colour. The number of branches and the amount of defective wood can be assessed even more accurately by measuring the wood meal 322 for its spectrum.

Figure 5:
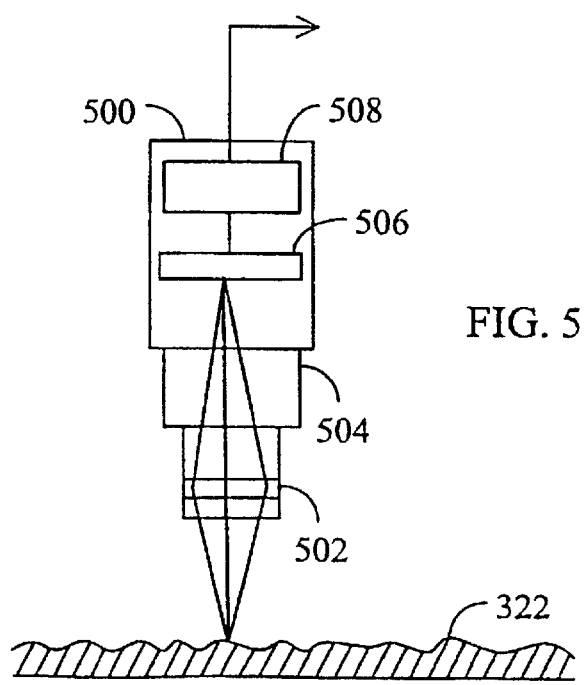
FIG. 5 shows a detector.
Figure 4:
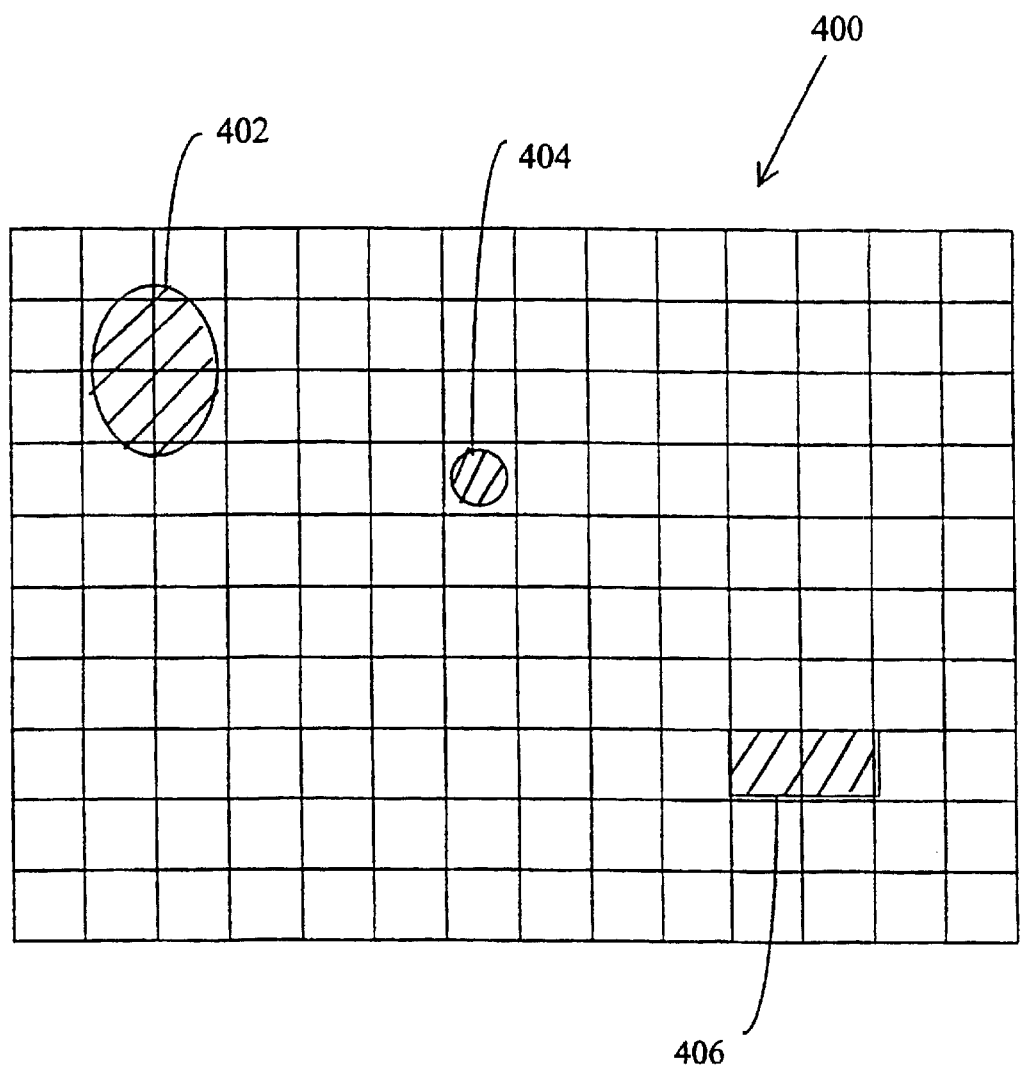
FIG. 4 shows the matrix surface of a detector.

Whatever measurements can be conducted with the measuring device 332 depends on the detector 330, which is now examined with reference to FIGS. 4 and 5. The actual detection surface of a detector 500, for example a video or line camera, can be constituted by a pixel matrix 400 or a pixel line. In the inventive solution, the reflection density of wood powder can also be determined without imaging optics 502, but most preferably the camera is provided with an objective constituted by lenses for making a real image of the wood meal or powder on the pixels of the detector 500. For the determination of the reflection density of wood meal or pieces 6f bark or other such pieces distinguishable from sound wood it is sufficient to use a black-and-white camera, while the acquisition of colour information requires a colour camera.

In a preferred embodiment of the invention, a detector surface 506 is formed with an image, wherein the per se known pattern recognition methods applied in image processing are used for separating domains that are exceptional or different from sound wood in terms of the darkness, tint, or spectrum thereof. The surface area of such exceptional domains are compared with that of the entire image or the detector surface 506 for a result proportional to the amount of bark or the like. Thus, the quality of wood is determined by measuring the wood quality in terms of pixels. In the visualization of FIG. 4, the exceptional or extraordinary matter is found in three sites 404, 404, and 406. The exceptional doamin 402 covers effectively 4 pixels, the exceptional domain 404 covers a single pixel, and the exceptional doamin 406 covers two pixels. Thus, the exceptional domains have a total area of about 7 pixels. Since the matrix has a total area of 10×14=140 pixels, the exceptional domain covers a share of the total which is 7/140=0.05. In reality, the measuring area of a matrix surface can be for example 500×500 pixels. If the size of an image is e.g. 500×500 pixels, the image field has a "surface area" of 250000 pixels. The image processing methods are readily capable of separating domains with a minimum size of 1–4 pixels from an image taken of a homogeneous matter. Consequently, the method has a theoretical responsivity which in the case of a single image is better than 0.0016% (=4/250000). In addition, the responsivity can be imporved further by increasing the number of images.

Information regarding the spectrum of wood powder is obtained by means of spectroscopy. For example, the solution shown in FIG. 5 has been implemented by using a spectrograph, such as a.o. SPECIM, a spectrograph called ImSpector, manufactured by Spectral Imaging Ltd. The apparatus comprises a detector surface 506 constituted by a pixel matrix for visualizing an object to be imaged by means of an objective 502. The detector surface 506 is functionally linked with an electronic circuit 508, which produces an electrical signal consistent with optical radiation received by the detector surface 506 to be forwarded to a measuring device. Between the imaging objective 502 and the pixel matrix 506 of the camera is a prism-lattice-prism component 504 for diffusing the object-emitted optical radiation into a spectrum. The actual image of an object is a single row matrix line (e.g. the x axis of an orthogonal xy coordinate system), and the spectrum of each aligned pixel spreads out onto pixels located laterally of the matrix (e.g. the y axis of an orthogonal xy coordinate system). As wood meal or powder is progressing on a conveyor belt, it is possible to image random parts of the wood meal at random moments, whereby the wood meal can be analyzed statistically for its reflection density, colour, and/or spectrum by using an automated data processing program of a computer.

In a solution of the invention, it is also possible that some of the software typically housed in the measuring block 332 be allocated also to the detector 330, 500. Thus, for example, the smart camera 330, 500 is used for selecting optical bands from the spectrum, which are transferred to the measuring device 332 for processing.

Although the invention has been described above with reference to the example shown in the drawings, it is obvious that the invention is not limited thereto, but it can be subjected to a multitude of modifications within the inventive concept set forth in the annexed claims.

What is claimed is:

1. A method for measuring the quality of wood, in which method the wood is constituted by timber which, in addition to a pure body (100), includes at least a bark component (102) and knot components (106), which differ from the pure body (100) in terms of optical properties thereof, the method involving the barking of logs (202, 302), characterized in that at least some of barked tree trunks (208, 308) are turned into a wood powder (212, 322);

the wood powder (212, 322) is illuminated with optical radiation; and the quality of wood is measured by means of the optical radiation in such a way, that the wood powder is used for making a pixel-compiled real image thereof, and the wood powder has its quality determined by means of pixel-specific optical properties.

2. A method as set forth in claim 1, characterized in that the quality of wood is measured by barking purity, whereby optical radiation is used for measuring the bark content of wood.

3. A method as set forth in claim 1, characterized in that the quality of wood is measured by a knot content, whereby optical radiation is used for measuring the knot content of wood.

4. A method as set forth in claim 1, characterized in that the logs (202, 302) include not only the bark component (102) and the knot component (106) but also defective wood (108) different from the pure body (100) in terms of its optical properties, and the quality of wood is measured by the amount of the defective wood (108), whereby optical radiation is used for measuring the amount of the defective wood (108).

5. A method as set forth in claim 1, characterized in that the wood powder (212, 322) is measured by means of optical radiation at a multitude of points for the statistical processing of wood quality.

6. A method as set forth in claim 1, characterized in that the barked trees (308) are chipped and the wood powder (322) is formed from chips (319).

7. A method as set forth in claim 1, characterized in that the logs (302) are barked and chipped for pulping, the chips are adapted to give a chip sample (319) which is worked into the wood powder (322), and the pulping is controlled by means of the determined wood quality.

8. A method as set forth in claim 2, characterized in that the determined barking purity of logs is used for controlling the barking process.

9. A method as set forth in claim 1, characterized in that the wood powder (212, 322) is measured by means of optical radiation for the reflection density of the wood powder (212, 322).

10. A method as set forth in claim 1, characterized in that the wood powder (212, 322) is measured by means of optical radiation for the colour of the wood powder (212, 322).

11. A method as set forth in claim 1, characterized in that the wood powder (212, 322) is used for making a real image thereof by means of imaging optics (502), and the quality of wood is determined from the real image.

12. A method as set forth in claim 11, characterized in that there is used a black-and-white real image, and the real image is used for measuring the quality of wood by means of dark and light constituent.

13. A method as set forth in claim 11, characterized in that there is used a colour real image, and the colour real image is used for measuring the quality of wood by means of colour differences.

14. A method as set forth in claim 11, characterized in that imaging spectroscopy is used for compiling spatial spectral data regarding the wood powder (212, 322), by means of which the quality of wood is determined.

15. A method as set forth in claim 11, characterized in that the determination of wood quality is performed from a real image automatically by using an image processing program.

16. A method as set forth in claim 1, characterized in that the wood powder (212, 322) is provided with such a size distribution that the essentially largest powder particles of the wood powder (212, 322) have a diameter of no more than a few centimeters.

17. A method as set forth in claim 1, characterized in that the wood powder (212, 322) is illuminated with visible light.

18. A method as set forth in claim 1, characterized in that the quality of wood is measured by receiving optical radiation from the wood powder (212, 322) with a video camera (500) and by processing a signal from the video camera (500) with a computer (336).

19. A measuring arrangement for the quality of wood, wherein the wood is constituted by timber which, in addition to a pure body (100), includes at least a bark component (102) and knot components (106), having optical properties that are different from those of the pure body (100), said measuring arrangement comprising a stripper (204, 304) for the barking of logs (202, 302), characterized in that the measuring arrangement is adapted to produce wood powder (212, 322) from barked trees (208, 308);

the measuring arrangement comprises a detector (220, 330) responsive or sensitive to optical radiation;

the measuring arrangement comprises a measuring device (222, 332); and the detector (220, 330) is adapted to receive optical radiation from the direction of the wood powder (212, 322) and to supply the measuring device (222, 332) with a signal consistent with the optical radiation, and the measuring device (222, 332) is adapted to measure the wood powder (212, 322) by means of an optical-radiation based signal coming from the detector (220, 330) and to determine the quality of wood in such a way that the detector (220, 330) is adapted to produce a pixel-compiled real image of the wood powder (212, 322), and the measuring device (222, 332) is adapted to determine the quality of the wood powder (212, 322) by means of pixel-specific properties.

20. An arrangement as set forth in claim 19, characterized in that the quality of wood refers to barking purity, whereby the measuring device (222, 332) is adapted to determine the bark content of wood.

21. An arrangement as set forth in claim 19, characterized in that the quality of wood refers to a knot content, whereby the measuring device (222, 332) is adapted to determine the knot content of wood.

22. An arrangement as set forth in claim 19, characterized in that the log (202, 302) includes not only the bark component (102) and the knot component (106) but also defective wood (108), having optical properties that are different from those of the pure body (100), and the quality of wood refers to the amount of the defective wood (108), whereby the measuring device (222, 332) is adapted to determine the amount of the defective wood (108).

23. An arrangement as set forth in claim 19, characterized in that the arrangement is adapted to chip the barked trees (208, 308) and to produce the wood powder (212, 322) from the chips.

24. An arrangement as set forth in claim 19, characterized in that the arrangement is adapted to bark and chip the logs (202, 302) for pulping, the arrangement is adapted to take a chip sample (319) from the chips which the arrangement is adapted to turn into the wood powder (322), and the arrangement is adapted to control a pulp digester (3314) by means of the determined wood quality.

25. An arrangement as set forth in claim 19, characterized in that the arrangement is adapted to control the stripper (304) by means of the determined barking purity.

26. An arrangement as set forth in claim 19, characterized in that the measuring device (222, 332) is adapted to measure the wood powder (212, 322) for its reflection density by means of optical radiation.

27. An arrangement as set forth in claim 19, characterized in that the measuring device (222, 332) is adapted to measure the wood powder (212, 322) for its colour by means of optical radiation.

28. An arrangement as set forth in claim 19, characterized in that the detector (220, 330) is a camera, comprising an imaging optics (502) and adapted to compile a real image of the wood powder (212, 322) by means of optical radiation, and the measuring device (222, 332) is adapted to determine the quality of wood from the real image compiled by the detector (220, 330).

29. An arrangement as set forth in claim 28, characterized in that the arrangement is adapted to use a black-and-white real image, and the measuring device (222, 332) is adapted to measure the quality of wood from the real image by means of a dark and light shade.

30. An arrangement as set forth in claim 28, characterized in that the detector (220, 330) is a colour camera, the arrangement is adapted tu use a colour real image, and the measuring device (222, 332) is adapted to measure the quality of wood from the colour real image by means of colour differences.

31. An arrangement as set forth in claim 28, characterized in that the camera (220, 330) comprises a spectrograph (504), which is adapted to compile a single-row real image and a spectral distribution of the wood powder (212, 322), and the measuring device (222, 332) is adapted to measure the quality of wood from the real image and the spectral distribution.

32. An arrangement as set forth in claim 19, characterized in that the measuring device (222, 332) is adapted to measure the wood powder (212, 322) optically at a plurality of points, and the measuring device (222, 332) is adapted to determine the quality of wood statistically by means of a plurality of measurements.

33. An arrangement as set forth in claim 19, characterized in that the arrangement is adapted to produce the wood powder (212, 322), which is distributed in terms of its size, such that the essentially largest powder particles of the wood powder (212, 322) have a diameter of no more than a few centimeters.

34. An arrangement as set forth in claim 19, characterized in that the measuring arrangement comprises an illuminator (218, 328) which produces optical radiation.

\* \* \* \* \*